US00PP25831P2

(12) United States Plant Patent
Zaiger et al.

(10) Patent No.: US PP25,831 P2
(45) Date of Patent: Aug. 25, 2015

(54) PEACH TREE NAMED 'RICH FIRE'

(50) Latin Name: *Prunus persica*
Varietal Denomination: Rich Fire

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 25 days.

(21) Appl. No.: 13/999,622

(22) Filed: Mar. 14, 2014

(51) Int. Cl.
*A01H 5/08* (2006.01)

(52) U.S. Cl.
USPC ..... Plt./197

(58) Field of Classification Search
USPC ..... Plt./197
CPC ..... A01H 5/0868; A01H 5/0837; A01H 5/08
See application file for complete search history.

*Primary Examiner* — Kent L Bell

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of large size fruit.
3. Fruit with an attractive red skin color.
4. Fruit with firm, yellow flesh.
5. Fruit with very good flavor and eating quality.
6. Fruit with good handling and storage quality.

1 Drawing Sheet

Botanical designation: *Prunus persica.*
Variety denomination: 'RICH FIRE'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of peach trees, which are known to us, and mentioned herein, 'Rich Lady' Peach (U.S. Plant Pat. No. 7,290), 'Super Rich' Peach (U.S. Plant Pat. No. 9,860) and our proprietary non-patented peach seedlings '177LE421' and '57EE47'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. as a selected seedling from open pollinated seed of our proprietary non-patented peach seedling with the field identification number '177LE421'. The seed parent (177LE421) originated as a first generation cross between 'Rich Lady' Peach (U.S. Plant Pat. No. 7,290) and our proprietary non-patented peach seedling selection '57EE47'. A large number of these open pollinated seedlings were budded on established trees of 'Nemaguard' Rootstock (non-patented), to enhance earlier fruit production. Under close and careful observation the present seedling exhibited desirable tree and fruit characteristics and was selected in 1998 for additional asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous, upright growth and a regular and productive bearer of large, yellow flesh, clingstone fruit. The fruit is further characterized by having an attractive red skin color, very good flavor and eating quality with a good balance between acid and sugar. In comparison to its seed parent '177LE421' peach (non-patented) the fruit of the new variety is larger in size. In comparison to the commercial variety 'Super Rich' Peach (U.S. Plant Pat. No. 9,860) the fruit of the new variety has firmer flesh and is approximately 13 days later in maturity.

DESCRIPTION OF PHOTOGRAPH

The accompanying color photographic illustration shows typical specimens of the foliage and fruit of the present new peach variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 13 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 13 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with type and fertility of soil and climatic conditions.

*Form*.—Upright, usually pruned to vase shape.

*Branching habit*.—Upright, crotch angle approximately 30°, increases with heavy crop load.

*Productivity*.—Productive, thinning and spacing necessary for desired market size fruit. Number of fruit set varies with climatic conditions during blooming period.

*Bearer*.—Regular, has had adequate fruit set 11 consecutive years. No alternate bearing observed.

*Fertility*.—Self fertile.

*Density*.—Medium dense, usually pruned to vase shape to increase sunlight to center of tree to enhance health of tree and improve fruit color.

*Hardiness*.—Hardy in all stone fruit growing areas of California. Tree grown in USDA Hardiness Zone 9. Winter chilling requirement approximately 750 hours at or below 45° F.

Trunk:

*Size*.—Medium, average circumference 55.9 cm at 38.1 cm above ground on an 13 year old tree.

*Stocky*.—Medium stocky.

*Texture*.—Medium shaggy, roughness increases with age.

*Color*.—Varies from 2.5Y 5/2 to 5Y 5/2.

Branches:

*Size*.—Medium. Average circumference 19.3 cm at 1.2 meters above ground. Crotch angle approximately 30°, increases with heavy crop load.

*Surface texture*.—New growth relatively smooth. Mature growth medium rough, becomes rougher with age.

*Lenticels*.—Average 16 in a 25.8 sq cm area of branch. Average length 5.9 mm. Average width 2.7 mm. Color varies from 10YR 5/8 to 10YR 5/10.

*Color*.—New growth varies from 5GY 6/6 to 5R 3/6. Old growth varies from 10YR 2/2 to 10YR 3/4, varies with age of growth.

Leaves:

*Size*.—Large. Average length 154.7 mm. Average width 45.2 mm.

*Form*.—Lanceolate.

*Apex*.—Acuminate.

*Base*.—Cuneate.

*Margin*.—Crenate.

*Thickness*.—Medium.

*Surface texture*.—Upper surface relatively smooth, slightly indented over midrib and leaf veins, glabrous. Lower surface relatively smooth, except for small ridges created by midrib and pinnate venation, glabrous.

*Petiole*.—Average length 13.3 mm. Average width 1.8 mm. Longitudinally grooved. Surface glabrous. Color varies from 5GY 5/8 to 5GY 5/6.

*Glands*.—Type — reniform. Size — large. Average length 1.5 mm. Average diameter 0.6 mm. Average number 3, varies from 2 to 4. Located primarily on base of leaf blade and upper portion of the petiole. Color varies from 10YR 3/4 to 10YR 3/6.

*Stipules*.—Average number 2. Average length 4.5 mm. Margin — pectinate. Color varies from 5GY 5/8 to 5GY 6/8.

*Color*.—Upper surface varies from 5GY 3/6 to 5GY 3/4. Lower surface varies from 5GY 4/4 to 5GY 5/4.

Flower buds:

*Size*.—Large. Average length 19.9 mm. Average diameter 11.9 mm.

*Hardiness*.—Hardy with respect to California winters.

*Form*.—Plump, conical becoming elongated just before opening.

*Pedicel*.—Average length 3.9 mm. Average width 1.4 mm. Color varies from 5GY 6/6 to 5GY 6/8.

*Color*.—Varies from 5RP 7/10 to 7.5RP 7/6.

Flowers:

*Blooming period*.—Date of First Bloom Feb. 28, 2013. Date of Petal Fall Mar. 9, 2013, varies slightly with climatic conditions.

*Size*.—Large, showy. Average height 24.8 mm. Average diameter 54.3 mm.

*Petals*.—Normally 5, alternately arranged to sepals. Size — large. Average length 27.0 mm. Average width 25.9 mm. Form — orbicular, narrows at point of attachment. Arrangement — free. Margin — sinuate. Color varies from 5RP 8/4 to 5RP 7/6, fades with age of flower. Both upper and lower surface glabrous.

*Sepals*.—Normally 5, alternately arranged to petals. Size — large. Average length 6.7 mm. Average width 6.6 mm. Shape — ovate. Margin — entire. Color — upper surface varies 5GY 5/8 to 7.5R 3/6. Lower surface 7.5R 2/6. Upper surface glabrous, lower surface pubescent.

*Stamens*.—Average number per flower 52. Average length 19.3 mm. Filament color varies from N 9.5/ (white) to 5RP 5/10. Anther color varies from 5Y 7/8 to 7.5R 3/10.

*Pollen*.—Self fertile. Color varies from 2.5Y 7/10 to 5Y 7/10.

*Pistil*.—Normally one. Surface — pubescent. Average length 19.7 mm. Stigma height an average of 2.5 mm below anthers. Color varies from 7.5Y 8/6 to 10Y 8/6.

*Fragrance*.—Wanting.
*Color*.—Varies from 5R 9/2 to 5RP 6/8.
*Number flowers per flower bud*.—One.
*Pedicel*.—Average length 5.5 mm. Average width 1.5 mm. Color varies from 5GY 5/6 to 5GY 5/8.

Fruit:
*Maturity when described*.—Firm ripe.
*Date of first picking*.—May 25, 2013.
*Date of last picking*.—Jun. 4, 2013, varies slightly with climatic conditions.
*Size*.—Large. Average diameter axially 65.4 mm. Average transversely in suture plane 71.1 mm. Average weight 198.8 grams, varies slightly with fertility of the soil, amount of thinning and climatic conditions.
*Form*.—Globose.
*Suture*.—Nearly smooth.
*Ventral surface*.—Nearly smooth.
*Apex*.—Rounded to slightly retuse.
*Base*.—Retuse.
*Stem cavity*.—Rounded to slightly elongated in suture plane. Average depth 4.7 mm. Average diameter 8.7 mm.

Stem:
*Size*.—Small. Average length 11.3 mm. Average diameter 2.4 mm.
*Color*.—Varies from 5GY 6/8 to 5GY 5/6.

Flesh:
*Ripens*.—Fairly even, some fruit slightly earlier at the apex.
*Texture*.—Firm, meaty, crisp.
*Fibers*.—Few, small, tender.
*Firmness*.—Firm, comparable to other commercial peach varieties.
*Aroma*.—Slight.
*Amydgalin*.—Undetected.
*Eating quality*.—Very good.
*Flavor*.—Very good, good balance between acid and sugar.
*Juice*.—Moderate amount, enhances flavor.
*Brix*.—Average Brix 12.8°, varies slightly with amount of fruit per tree and climatic conditions.
*Color*.—Varies from 10YR 7/8 to 10YR 7/10.
*Pit cavity*.—Average length 35.5 mm. Average width 26.5 mm. Average depth 14.3 mm. Color varies from 10YR 6/10 to 10YR 6/12.

Skin:
*Thickness*.—Medium.
*Surface*.—Smooth.
*Pubescence*.—Moderate amount, very short.
*Tendency to crack*.—None.
*Color*.—Ground color varies from 2.5Y 8/10 to 5Y 8/6. Overspread with 5R 4/10 to 7.5R 3/8.
*Tenacity*.—Tenacious to flesh.
*Astringency*.—Undetected.

Stone:
*Type*.—Clingstone.
*Size*.—Large. Average length 34.5 mm. Average width 26.2 mm. Average thickness 25.2 mm.
*Form*.—Ovoid.
*Base*.—Flat.
*Apex*.—Round.
*Surface*.—Pitted throughout, pits vary from round to elongated.
*Sides*.—Unequal, one side extending further from suture plane.
*Ridges*.—Extend from base to apex.
*Tendency to split*.—None.
*Color*.—Varies from 7.5YR 6/8 to 10YR 6/8 when dry.

Kernel:
*Size*.—Large. Average length 19.8 mm. Average width 11.0 mm. Average depth 6.0 mm.
*Form*.—Ovoid.
*Viability*.—Partially viable, incomplete embryo development in some fruit.
*Skin color*.—Varies from 5Y 9/4 to 7.5Y 9/2.

Use: Dessert.
*Market*.—Local and long distance.

Keeping quality: Good, held firm in cold storage for 3 weeks at 38° to 42° F. without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

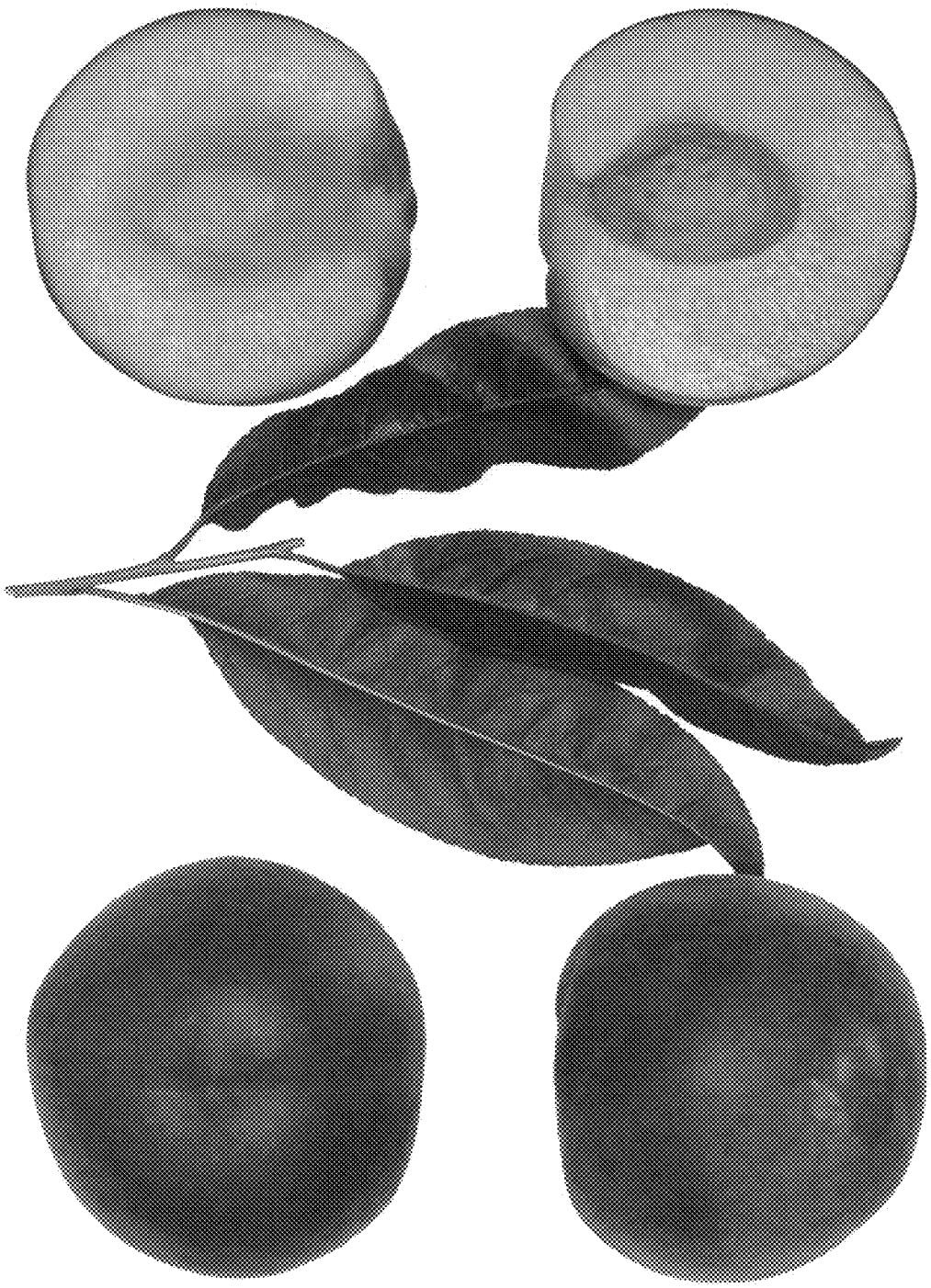

* * * * *